United States Patent [19]

Freundlich et al.

[11] Patent Number: 4,857,454

[45] Date of Patent: Aug. 15, 1989

[54] SPECTROPHOTOMETRIC METHOD FOR KINETIC ABSORBANCE MEASUREMENTS IN TWO-PHASE ENZYME IMMUNOASSAY AND APPARATUS THEREFOR

[75] Inventors: Lawrence F. Freundlich, New Hyde Park, N.Y.; Vadiraja V. Murthy, Teaneck, N.J.; Arthur Karmen, Manhasset, N.Y.

[73] Assignee: a Division of Yeshiva University Albert Einstein College of Medicine of Yeshiva University, Bronx, N.Y.

[21] Appl. No.: 36,360

[22] Filed: Apr. 9, 1987

[51] Int. Cl.$^4$ .................. G01N 33/53; G01N 33/557; G01N 33/546; G01N 33/543

[52] U.S. Cl. ......................................... 435/7; 435/808; 436/517; 436/807; 436/533; 436/534; 436/518; 356/427

[58] Field of Search ................. 435/7, 17, 21, 808; 436/517, 534, 533, 518, 523, 527, 531, 807, 808, 164; 356/427

[56] References Cited

U.S. PATENT DOCUMENTS

| | | | |
|---|---|---|---|
| 4,027,979 | 6/1977 | Komarniski | 356/427 X |
| 4,135,818 | 1/1979 | Kent et al. | 356/427 X |
| 4,205,954 | 6/1980 | Babson | 436/517 |
| 4,283,141 | 8/1981 | Stockdale et al. | 356/427 X |
| 4,320,977 | 3/1982 | Matsumoto | 356/427 |
| 4,372,683 | 2/1983 | Sternberg | 356/427 X |
| 4,681,742 | 7/1987 | Johnson et al. | 436/809 X |
| 4,714,672 | 12/1987 | Rokugawa et al. | 436/517 X |
| 4,767,600 | 8/1988 | Vicario | 435/301 X |

OTHER PUBLICATIONS

Myrtle J., et al., "Creatine Kinase MB Isoenzyme Quantitation in Serum by Simultaneous Immunoenzymetric Assay", Clin. Chem., 29, 1232, (1983).

Sheehan M., et al., "Evaluation of an Immunoenzymetric Assay for Creatine Kinase Isoenzyme MB (CK-MB)," Clin. Chem., 31, 160-161, (1985).

Boch J., et al., "False Positive Immunometric Assays Caused by Anti Immunoglobulin Antibodies: a Case Report," Chin. Chem. Acta., 147, 241-245, (1985).

Procedure Supplied with Tandem-E CKMB Immunoenzymetric Assay Kit of Hybritech Inc., San Diego, Calif. 92121, (date unknown).

Manual Supplied with Beckman Series 30 UV-Visible Spectrophotometers of Beckman Instruments, Inc., Scientific Instruments Division, Irvine, Calif. 92713, (1977).

Primary Examiner—Esther M. Kepplinger
Assistant Examiner—Randall E. Deck
Attorney, Agent, or Firm—Amster, Rothstein & Ebenstein

[57] ABSTRACT

A method is described for kinetic measurement of enzyme activity bound to a solid matrix which improves both the sensitivity and speed of one immunoassay method. The immunoassay typically consists of reaction of the analyte with two specific antibodies, one fixed to the surface of a polymeric bead or wall of a test tube, the other added in solution and labeled by covalent coupling to an enzyme. By reaction between analyte and both antibodies, the enzyme-labeled antibody becomes fixed to the surface in a quantity proportional to the quantity of the analyte. After washing sufficiently to remove unreacted enzyme-labeled antibody, fixed enzyme activity is measured by incubation with a substrate and measurement of the rate of the reaction catalyzed. Fixation of the enzyme causes the reaction products to be localized near the surface. To measure the concentration of reactant or product repeatedly during the reaction, the solution must be mixed before each measurement, which can interfere with the measurement. In the prior art, the reaction is stopped after incubation and the product measured once. The method and apparatus disclosed here provides stirring and measurement away from the surface, and thus permits repeated measurement during the reaction. This kinetic assay can be performed more rapidly and sensitively than assays based on a single measurement.

10 Claims, 2 Drawing Sheets

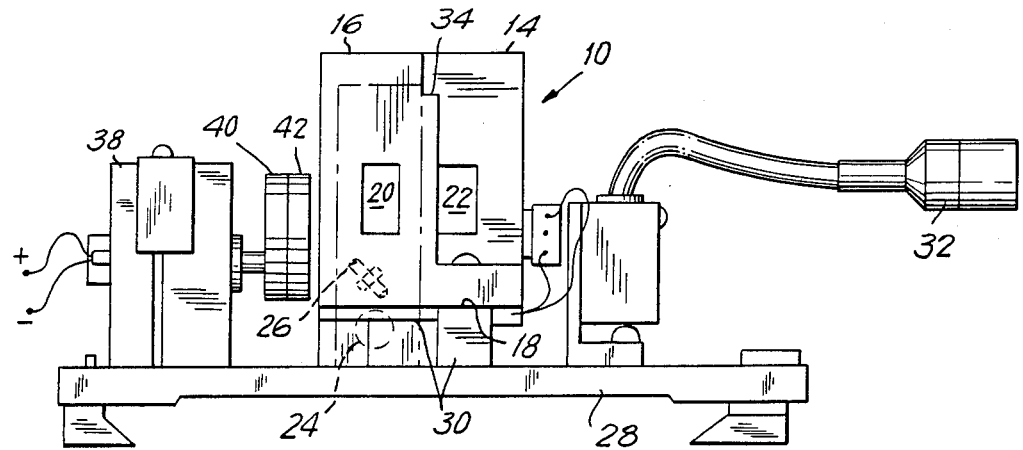
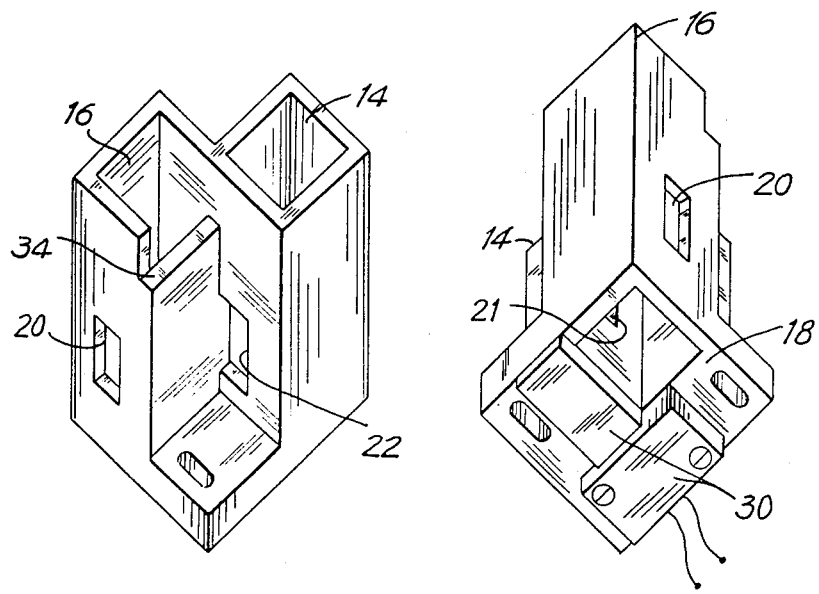
FIG. 1
FIG. 2
FIG. 3

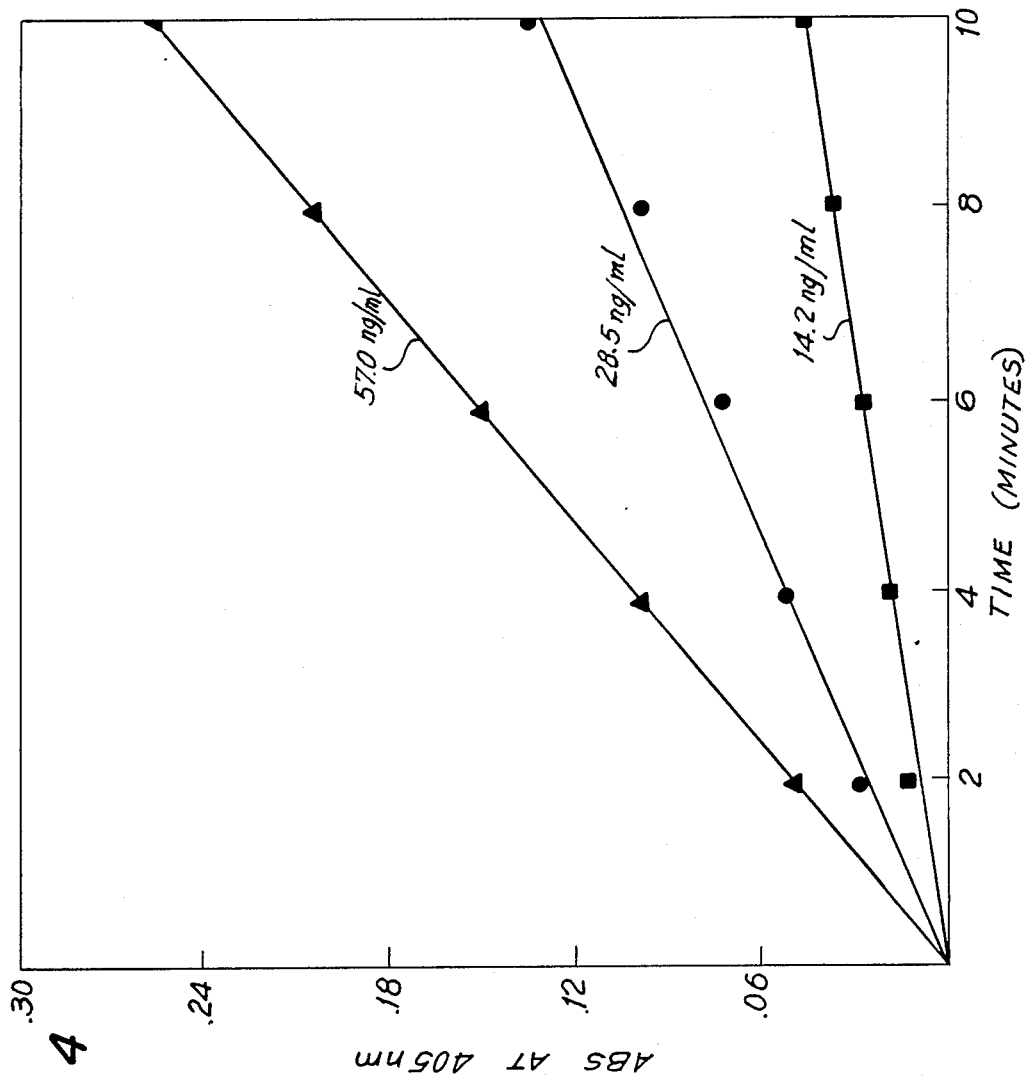

SPECTROPHOTOMETRIC METHOD FOR KINETIC ABSORBANCE MEASUREMENTS IN TWO-PHASE ENZYME IMMUNOASSAY AND APPARATUS THEREFOR

BACKGROUND OF THE INVENTION

The present invention relates generally to a method and system for measuring the activity of enzyme bound to a solid surface, and more particularly to a spectrophotometric method and system for absorbance measurements in two-phase enzyme immunoassays.

Many immunoassay methods currently in favor in the clinical laboratory require, as their last step, spectrophotometric measurement of the activity of an enzyme covalently linked as a label to one of the reactants in the antigen-antibody reaction. In one form of such immunoassay, an antibody specific for the analyte is immobilized or fixed on the surface of a solid phase, such as a polymeric bead or the wall of a test tube. When incubated with the analyte, the antibody fixes the analyte through an antigen-antibody reaction. A second antibody, labeled by covalent linkage with an enzyme and also directed against the analyte, is added in solution to the incubation mixture. Through its reaction with the analyte, it too becomes bound to the surface. The quantity of enzyme bound is then directly proportional to the quantity of analyte. This enzyme is generally measured by its activity: the rate of the reaction is catalyzes when incubated with a predetermined concentration of its substrate under prescribed conditions. This rate, in turn, is measured by measuring the change in concentration with time of either the product of the reaction or the precursor reactant. Although many methods can be used to measure the activity of an enzyme in solution, procedures for measuring the enzyme bound to a surface are comparatively more difficult and subject to interference by the surface and by the need to supply more than the usual stirring or mixing of the reaction mixture. It is toward improving the measurement of this enzyme activity that the invention described here is directed.

An example of an assay employing this approach is the "TANDEM-E CKMB" immunoenzymetric assay (available from Hybritech Inc., San Diego, Calif. 92121), which is used to measure the serum concentration of one of the isoenzymes of creatine kinase (CK). CK, an enzyme that catalyzes the reversible phosphorylation of creatine by adenosine triphosphate, appears in serum of patients in higher than usual concentrations in the hours and days following acute myocardial infarctions. Its measurement is used in the diagnosis and monitoring of patients with this disease. The different isoenzymes of CK are composed of the two enzymatically active subunits, termed M and B, in the three possible dimeric combinations: MM, MB and BB. The different isoenzymes are separable by electrophoresis and chromatography and may also be distinguished by reaction with specific antibodies. They are found in different concentrations and ratios in various tissues of the body: the MM chiefly in skeletal and cardiac muscle, the MB chiefly in cardiac muscle, and the BB chiefly in brain and tissues of endodermal origin. In blood serum, CK is in higher than usual concentration in diseases involving ischemia or destruction of tissues in which the enzyme is in high concentration. In the hours and days after the onset of ischemia and destruction of cardiac muscle that is characteristic of acute myocardial infarction, many-fold increases in concentration of total CK, CK-MM, and CK-MB are characteristically measurable in serum. Since similar elevations of serum CK-MM, the major component of total CK activity, are noted in many other conditions that affect skeletal muscle, and these are much more frequent, elevation of CK-MB isoenzyme is much more specific for myocardial infarction and for that reason more diagnostically useful.

In the Tandem assay procedure, serum is reacted with a plastic bead (the solid phase member) coated with a monoclonal antibody directed toward a unique antigenic site on the M subunit of the CK MB molecule, and with a second monoclonal antibody, labeled with an enzyme such as alkaline phosphatase, that is directed toward a different antigenic site on the B subunit of the same CK-MB molecule. In the presence of CK-MB, both antibodies react, sandwiching the CK MB between them, and the enzyme label of the second antibody becomes immobilzed on the surface of the bead.

The bead is then washed to remove unbound labeled antibody and the remaining bound enzyme label is measured by incubating the bead in a solution of its substrate for a period of some 30 minutes, at a controlled temperature (e.g. 37° C.). The reaction is then stopped and the quantity of substrate reacted is determined colorimetrically. With p-nitrophenyl phosphate, a commonly used substrate for the alkaline phosphatase labeling enzyme, the quantity of p-nitrophenol released is measured as the absorbance of the solution at 405nm, which is determined primarily by the concentration of p-nitrophenol. Through the sequence of antigen-antibody reactions described above, this absorbance is directly proportional to the concentration of CK-MB in the test sample.

The enzymatic reaction occurs at the surface where the labeling enzyme is bound. Unless the solution is stirred continuously, which is generally inconvenient, the reaction product tends to remain in high concentration near the surface and is not uniformly distributed throughout the incubation mixture. To measure the quantity of product produced, the "TANDEM-E CK MB" procedure, and indeed all of the other currently available two phase, enzyme linked immunoassay procedures, measure the absorbance only once, after the enzymatic reaction catalyzed by the labeling enzyme has progressed for a predetermined period of time. The reaction is then stopped, generally by dilution with reagents which change the pH of the mixture or remove a necessary cofactor such as magnesium ion by chelation. Once the reaction has been terminated, the solution is stirred to ensure that the measured product is uniformly distributed throughout the solution and the absorbance of the supernatant solution, away from the bead, is measured.

While offering some advantages, end point assays of enzyme activity present several important difficulties. First, the result cannot be read until the pre set incubation period is terminated, some 30 minutes after the start of the enzymatic reaction in the procedure described above. Second, when the concentration of reaction product is low, corresponding to a low concentration of analyte in the sample, interference caused by unavoidable background absorbance of the sample in the solution can become relatively significant; detection of small quantities of analyte then becomes of doubtful validity. This is the reason the reaction is generally allowed to proceed long enough to ensure production of substantial quantities of reaction product so that its concentration becomes high compared to those of interfering compounds. When the concentration of analyte is small, even this measure may not be completely effective. Third, assays made on the basis of single spectrophotometric measurements are inherently imprecise. Fourth, although conditions are chosen that favor constancy of the reaction rate upon which the enzyme activity is based, deviations from constancy cannot be detected when the assay is based on measurement at only one time.

Accordingly, it is an object of the present invention to provide a spectrophotometric method for kinetic absorbance measurements in two phase enzyme immunoassays.

Another object of the present invention is to provide such a method which allows the assays to be performed in less time than required for conventional end-point assays, with greater sensitivity, enhanced precision, and confirmation of constancy of reaction rate.

A further object of the present invention is to provide such a method which can be practiced on existing spectrophotometric systems with only minor physical modification.

Yet another object is to provide apparatus for performing such a method.

SUMMARY OF THE INVENTION

It has now been found that the above and related objects of the present invention are obtained in a method of enzyme-linked immunoassay in which the enzyme activity immobilized on a solid phase as a result of the antigen-antibody reaction is measured by kinetic spectrophotometry. The solution containing the enzyme and its substrate is agitated continuously t diffuse the product uniformly while its concentration is monitored.

In a preferred embodiment, the optical absorbance of the solution is monitored continously during the course of the reaction for sufficient time to ensure reliable measurement of the enzyme activity. Uniformity of concentration is accomplished by gentle stirring that is typically accomplished by means of a magnetically driven vane disposed below the level of the light path of the spectrophotometer. The solid phase is typically the surface of a bead formed of glass or organic polymer or a defined portion of the surface of the wall of the vessel containing the reaction mixture.

An example of an application of the invention is in the assay of creatine kinase MB isoenzyme by its reaction with two specific antibodies, one fixed to the surface of the solid phase, the other supplied in solution and labeled by covalent bonding to alkaline phosphatase. Following removal of unreacted reagent enzyme by washing, the activity of the reacted alkaline phosphatase enzyme is measured by incubating the solid phase with a substrate solution containing p-nitrophenyl phosphate and continuously monitoring the rate of production of p nitrophenol by the rate of change of absorbance at 405 nm.

More particularly the spectrophotometric method for kinetic absorbance measurements in a two-phase enzyme immunoassay comprises the steps of immobilizing a labeling enzyme on the surface of a solid phase member by an antibody-antigen reaction involving the subject enzyme and incubating the solid phase member in an enzyme substrate solution. During incubation, at least intermittently, the development of absorbance in the solution is spectrophotometrically monitored while agitating the solution to diffuse the developed absorbance (i.e., the absorbing material) throughout the solution.

In a preferred embodiment, the agitating of the solution and the monitoring of the absorbance development is continuous during incubation. The solution is agitated gently to avoid the formation of bubbles therein. The agitation of the solution is caused by a stirrer, typically a magnetically driven vane, disposed below the level of the path of the light beam of the spectrophotometer, the stirrer agitating both the solution and the solid phase member. Preferably, the stirrer intermittently directly physically contacts the solid phase member to maintain the same in motion below the level of the path of the light beam of the spectrophotometer.

The solid phase member is preferably a bead, the agitation of the solution and the action of the stirrer keeping the same in motion. The bead is typically formed of glass or plastic. In the method of the present invention, the subject enzyme is preferably creatine kinase MB isoenzyme, the labelling enzyme is alkaline phosphatase, the enzyme substrate is p-nitrophenyl phosphate, and the development of absorbance in the solution is spectrophotometrically monitored by measurement of the absorbance of p nitrophenol at 405 nm.

Another aspect of the present invention comprises a spectrophotometric system for kinetic absorbance measurements in a two phase enzyme immunoassay. The system comprises means for spectrophotometrically monitoring at least intermittently the development of optical absorbance in an incubating solution containing both a liquid phase enzyme substrate and a labeling enzyme immobilized on the surface of a solid phase member by an antibody-antigen reaction involving the subject molecule. The system further includes means for agitating the incubating solution to diffuse the developed absorbance throughout the solution.

In a preferred embodiment, the agitating means comprises a stirrer and magnetic means for driving the stirrer while maintaining the stirrer below the level of the path of the light beam of the monitoring means. The stirrer is preferably a magnetically driven spinning vane comprising a cylinder having a nut centrally mounted thereon, the nut being adapted to intermittently directly physically contact the solid phase member to maintain the same in motion below the level of the path of the light beam of the monitoring means.

BRIEF DESCRIPTION OF THE DRAWING

The above description, as well as further objects and features of the present invention, will be more fully understood by reference to the following detailed description of the presently preferred, albeit illustrative, embodiments of the present invention when taken in conjunction with the accompanying drawing wherein:

FIG. 1 is a side elevation view of the cell (in phantom-line) and cell holder of a spectrophotometer useful in the practice of the present method;

FIG. 2 is a top isometric view of the cell holder of FIG. 1;

FIG. 3 is a bottom isometric view of the cell holder of FIG. 1; and

FIG. 4 is a graph of light absorbance at 405 nM against incubation time in minutes for solutions of varying concentrations of the subject enzyme.

DETAILED DESCRIPTION OF THE PREFERRED EMBODIMENTS

According to the present invention, a labeling enzyme (such as alkaline phosphatase) is immobilized on the surface of a solid phase member (such as a glass or plastic bead) by an antibody-antigen reaction involving the analyte (such as CKMB). The immobilizing procedure utilized may be the same as in the "TANDEM-E" CKMB immunoenzymetric assay technique of Hybritech, Inc. For example, a plastic bead of 8 mm diameter is put into a test tube, the bead being coated with mouse monoclonal IgG (against the M subunit) in a buffer containing 0.1% sodium azide. Then, 100 ul of antibody conjugate is pipetted into the test tube. The antibody conjugate is mouse monoclonal IgG (against the B subunit) conjugated to bovine alkaline phosphatase in a protein matrix containing 0.1% sodium azide. Next, 100 ul of the specimen (human serum) is pipetted into the test tube, and the test tube is shaken. The solution is then incubated for one hour on a rotator at room temperature at 170 ±10 RPM. The bead is then washed with two milliliters of buffer three times. Finally, the bead is incubated in 200 ul of an enzyme substrate solution comprising an excess of p-nitrophenol phosphate, in buffer.

During the incubation of the bead or solid phase member in the enzyme substrate solution, at least intermittently the development of absorbance in the solution is spectrophotometrically monitored while the solution is agitated to diffuse the absorbing material throughout the solution. The agitation of the solution is a critical step in the present kinetic procedure because the absorbance develops on or very near the surface of the bead. In order to enable agitation of the solution while the developed absorbance is being monitored, a specially designed cell holder may be employed or the cell holder of a standard spectrophotometer may be appropriately modified as needed.

To carry out the invention, a conventional Beckman Series 35 UV-visible spectrophotometer (available from the Scientific Instruments Division of Beckman Instruments, Inc., of Irvine, Calif. 92713) was modified as illustrated in FIGS. 1-3 to enable the solution to be agitated while the color development was monitored. Referring now to FIG. 1 therein illustrated is a cell holder, generally designated by the reference numeral 10. The holder 10 defines a pair of diagonally aligned cell compartments, a reference cell compartment 14 for holding a cell containing a reference solution and a sample cell compartment 16 for a cell (shown in phantom-line) holding the sample to be tested. In the original equipment, the base 18 of the holder 10 supports the cells within their respective compartments 14, 16 so that the light beam of the spectrophotometer may travel, as directed by the vibrating mirror bridge, through its designated alternating paths, one path through entry window 20, the sample cell, and the exit window 21 of the sample cell compartment 16, and the other path through the entry window 22, the reference cell and exit window (not shown) of the reference cell compartment 14. It will be appreciated that if the solid phase member or bead 24 and a stirrer 26 were to be placed in the sample cell of an unmodified cell holder, one or both would intersect the path of the light beam passing through the sample cell between windows 20 and 21, giving erroneous absorbance readings. Accordingly, a legged frame or support 28 is secured to the cell holder 10, and the base 18 is cut away immediately below the sample cell compartment 16, so that the bottom of the sample cell falls substantially below the base 18 (about 1 centimeter) and onto frame 28, thereby situating bead 24 and stirrer 26 below the level of the windows 20, 21. This also requires that heating element 30 energized by electrical plug 32 (used to maintain the solutions in the cells at a standard temperature), previously at least partially vertically aligned with the sample cell compartment 16, be horizontally relocated as shown in FIG. 3 and that wall 34 of the sample cell compartment 16 be ground down as shown in FIGS. 1-3 to enable easy positioning and removal of the sample cell therein and therefrom.

In order to provide agitation, a magnetic micro stirrer 26 is placed in the sample cell. The stirrer is preferably a Teflon coated magnetic spinning vane formed of a cylinder, 12 mm in length and 2 mm in diameter, with a Teflon nut-like polygonal extension, 7 mm on each side, centrally mounted thereabout (Catalog No. 14 511-67 of the Fisher Scientific Co. of Springfield, N.J.). A small DC motor 38 is secured to the frame 28 adjacent the sample cell compartment 16. The motor 38 is a battery powered 1.5 volt, 25 microampere "mini-motor" (Catalog No. D40.872 of the Edmond Scientific Co. of Barrington, N.J.). A steel disk cam 40 (1.9 mm in diameter, 6 mm thick) is slipped over the motor shaft, and an external disk magnet 42 is then glued to the cam 40. The magnet 42 is preferably a cobalt disk magnet, 1.9 mm outside diameter and 6 mm thick (Catalog No. D30.962 of the Edmond Scientific Co. of Barrington, N.J.). The disk cam 40, and thus the disk magnet 42, is mounted eccentrically on the shaft of the motor 38 in such a manner that magnet 42 maintains the stirrer 26 below the level of the windows 20, 21, and, under the influence of the activated motor 38, agitates the enzyme substrate solution within the sample cell. The agitation is necessarily sufficiently gentle to avoid the formation of bubbles which would float past the windows 20, 21 and create false readings. The stirrer 26 is furthermore configured and dimensioned so that it is intermittently in direct physical contact with the bead 24, successive corners of the stirrer nut impinging downwardly on the bead and bouncing it off the bottom of the cell to impart to it a bouncing vertical motion, thereby to further ensure that the absorbing material developing in the region of the bobbing bead becomes dispersed throughout the solution in the sample cell.

The stirrer 26 during the monitoring of absorbance development is maintained above the bottom of the sample cell and at least partially above the solid phase member, but below the level of the path of the light beam of the spectrophotometer and intermittently directly physically contacting the solid phase member to maintain the same in motion below the level of the path of the light beam of the spectrophotometer during the monitoring of absorbance development.

Agitation of the solution and spectrophotometric monitoring of the absorbance development therein is preferably continuous throughout the incubation period—that is, from the time that the solid phase member begins to incubate in the enzyme substrate solution. Indeed, as the zero time or initial absorbance measurement is often a preferred reading, the solid phase member 24 and stirrer 26 are preferably already disposed in the sample cell with compartment 16, with the stirrer actuated, prior to the time that the enzyme substrate solution is added to the sample cell, thereby permitting an immediate initial reading. The readings are interpreted using appropriate calibration graphs formulated from use of the procedure on known analyte concentrations. Alternatively, intermittent spectrophotometric monitoring of the absorbance development may be performed by periodically switching the spectrophotometer on and off so as to give a series of readings over time. The solution must be agitated, however, during the monitoring periods and sufficiently before readings are taken to ensure adequate absorbance dispersal at the time of the monitoring.

In order to determine whether stirring of a solution in the presence of a plastic bead would have any effect on the absorbance measurements, continuous record over time of the absorbance at 405 nm of a series of dilute solutions (from 5.0 uM to 60.0 uM) of potassium dichromate were made. There were less than three milliabsorbance units of noise when the solutions were stirred, with no significant difference in absorbances due to the stirring alone.

The spectrophotometer used in the examples below may be of any conventional type such as a double beam, digital reading and recording instrument for measuring light levels at specified wave lengths. Light from a given source (usually a deuterium or tungsten incandescent lamp) is directed through a narrow bandpass filter or grating monochromator. The monochromatic light is then directed to the sample and reference via a vibrating mirror which displaces horizontally at a certain frequency. Therefore, this vibrating mirror allows light to pass into the sample and reference cell holders with a frequency equal to the displacement frequency of the mirror.

Light transmission through the cells is detected by a side-on multiplier phototube. The photocathode of this tube senses the photons of light passing through the sample and reference cells and generates a flow of electrons that is amplified by a series of dynodes within the tube. Finally, the electrons generated in the tube are captured at an anode that generates the voltage pulse proportional to the total number of electrons received. The current pulses generated by the sample and reference light levels to the multiplier phototube are then amplified and analyzed by a log converter. The log converter transforms the light transmission current values into absorbance values, where absorbance is equal to the logarithm of the reciprocal of transmittance. The output from the log converter is then displayed by a digital display and recorder. (If desired, the amplified signals can be displayed or displayed and recorded in a percentage transmission mode instead.)

EXAMPLE I

To test for proportionality of alkaline phosphatase activity to the quantity of CK-MB isoenzyme bound to the bead, graded quantities of CK-MB standard solutions (14.2, 28.5 and 57 ng/ml, respectively) were used according the Hybritech protocol. During incubation according to the procedure of the present invention, the solution was continuously agitated and the development of absorbance was intermittently spectrophotometrically monitored, with the results indicated in FIG. 4. As illustrated therein, the rates of production of p-nitrophenol were constant during the first ten minutes of incubation and were proportional to the concentration of CK MB isoenzyme added.

EXAMPLE II

To determine if stirring is necessary to promote uniform distribution of the colored p nitrophenol Example I is repeated except that there is no stirring of the solution during incubation. The apparent rate of p-nitrophenol production (as measured by absorbance) is significantly lower than indicated in Example I, thereby suggesting that stirring is indeed necessary to ensure uniform distribution of the color.

EXAMPLE III

To determine whether constant stirring of the solution is necessary or whether intermittent stirring would suffice, Example I is repeated except that agitation of the solution is not commenced until five minutes after the p-nitrophenol production reaction has commenced. Shortly after stirring is commenced, the absorbance measurements reach the same level as in Example I (where the solution was stirred from inception of the reaction), thereby indicating that intermittent stirring is sufficient for production of the colored reaction product.

Example III further indicates that the rate limiting step in Example II is not the access of the enzyme substrate to the labelling enzyme on the bead, but rather the limited diffusion of the p-nitrophenol product away from the bead and into the path of the light beam of the spectrophotometer in the absence of stirring.

The advantages of a kinetic assay of the present invention over a conventional end point assay are at least four in number. First, a kinetic assay can be performed rapidly and in less time than an end point procedure. Kinetic analysis virtually eliminates the obligatory incubation period required by the end point procedure and decreases the required time by as much as 90% (for example, three minutes for a kinetic assay versus 30 minutes for an end point assay). Second, a kinetic assay increases the sensitivity of the determination. Kinetic analysis minimizes the interference caused by background noise, thereby permitting the monitoring of lower concentrations of analyte (that is, subject enzyme). Third, a kinetic assay provides enhanced precision. A kinetic analysis can be viewed as a dynamic series of end-point analyses, and it is known that the precision of a given assay increases by the square root of the number of assays performed per analyte. Fourth, a kinetic assay confirms constancy of reaction rate. Such confirmation reduces the likelihood of false positive reactions caused by interfering chromogenic substances present in the mixture. The constancy of the reaction rate (as indicated by a straight line graph of absorbance against time) confirms that it is enzyme activity being measured rather than impurities.

The present invention comprises a spectrophotometric system for kinetic absorbance measurements in two-phase enzyme immunoassays. While the description has specifically concerned a spectrophotometric system for the determination of creatine kinase-MB (CK-MB) isoenzyme as the subject enzyme and took as its departure point the "TANDEM-E" CKMB immunoenzymetric assay technique of Hybritech, Inc., it should be appreciated that the kinetic assay technique of the present invention can presumably be adapted to any of the similar "Tandem" procedures as well as other known end-point assay techniques. At present, there are more than 50 two phase enzyme immunoassay kits employing end-point determinations commercially available from more than 10 corporate suppliers. These kits provide for the qualitative and/or quantitative determination of a multitude of analytes including viral antigens and antibodies, bacterial antigens and antibodies, serum drug and hormone concentrations and various tumor markers.

To summarize, it has been found that a uniform dispersement of developed absorbance ca be achieved with appropriate agitation of the bead and incubation solution, without detectibly increasing the noise. This paves the way for a kinetic assay procedure which can be performed rapidly and in less time than the conventional end point procedure, with greater sensitivity, reliability and precision.

Now that the preferred embodiments of the present invention have been shown and described in detail, various modifications and improvements thereon will become readily apparent to those skilled in the art. Accordingly, the spirit and scope of the present invention is to be limited only by the appended claims, and not by the foregoing specification.

What is claimed is:

1. A spectrophotometric method for kinetic absorbance measurements in a two phase enzyme immunoassay for an analyte comprising the steps of:
    (A) immobilizing a labeling enzyme on the surface of a solid phase member by an antibody-antigen reaction involving the analyte;
    (B) incubating the solid phase member in an enzyme substrate solution in a sample cell to produce a product; and
    (C) during incubation, at least intermittently spectrophotometrically monitoring the development of optical absorbance in the solution while agitating both the solution and the solid phase member with a stirrer to diffuse the substrate and product throughout the solution, the stirrer during the monitoring of absorbance development being maintained above the bottom of the sample cell and at least partially above the solid phase member, but below the level of the path of the light beam of the spectrophotometer and intermittently directly physically contacting the solid phase member to maintain the same in motion below the level of the path of the light beam of the spectrophotometer during the monitoring of absorbance development.

2. The method of claim 1 wherein the agitating of the solution is continuous during incubation.

3. The method of claim 2 wherein the monitoring of absorbance development is continuous during incubation.

4. The method of claim 1 wherein the solution is agitated in a manner to avoid the formation of bubbles therein.

5. The method of claim 1 wherein the stirrer is a magnetically driven vane.

6. The method of claim 5 wherein the stirrer comprises a cylinder having a polygonal extension centrally mounted thereon.

7. The method of claim 1 wherein the solid phase member is a bead.

8. The method of claim 7 wherein the bead is formed of glass or plastic.

9. The method of claim 1 wherein the analyte is creatine kinase MB isoenzyme.

10. The method of claim 1 wherein the labeling enzyme is alkaline phosphatase, the enzyme substrate is p-nitrophenyl phosphate, and the development of absorbance in the solution is spectrophotometrically monitored by measurement of the absorbance of p-nitrophenol at 405 nM.

* * * * *